United States Patent [19]

Pinchuk

[11] Patent Number: 5,575,818
[45] Date of Patent: Nov. 19, 1996

[54] ENDOVASCULAR STENT WITH LOCKING RING

[75] Inventor: Leonard Pinchuk, Miami, Fla.

[73] Assignee: Corvita Corporation, Miami, Fla.

[21] Appl. No.: 388,612

[22] Filed: Feb. 14, 1995

[51] Int. Cl.[6] ................................................. A61F 2/06
[52] U.S. Cl. ........................ 623/1; 623/12; 606/195
[58] Field of Search ............................. 623/1, 11, 12;
606/192, 194, 195, 108

[56] References Cited

U.S. PATENT DOCUMENTS

| | | | |
|---|---|---|---|
| 4,954,126 | 9/1990 | Wallsten | 623/1 |
| 5,061,275 | 9/1991 | Wallsten | 623/1 |
| 5,064,435 | 11/1991 | Porter | 623/12 |
| 5,197,978 | 3/1993 | Hess | 623/12 |
| 5,330,500 | 7/1994 | Song | 623/1 |
| 5,383,892 | 1/1995 | Cardon et al. | 623/12 |
| 5,395,390 | 3/1995 | Simon et al. | 623/1 |
| 5,397,355 | 3/1995 | Martin et al. | 623/12 |

FOREIGN PATENT DOCUMENTS

| | | | |
|---|---|---|---|
| 0587197 | 3/1994 | European Pat. Off. | 623/12 |
| 9112779 | 9/1991 | WIPO | 623/12 |
| 9424961 | 11/1994 | WIPO | 623/1 |

*Primary Examiner*—John G. Weiss
*Assistant Examiner*—Bruce E. Snow
*Attorney, Agent, or Firm*—David P. Gordon

[57] ABSTRACT

A tubular stent is provided with a braided structure having a body portion and an end portion, where the end portion has a higher pitch angle than the body portion, thereby forming a locking ring. If desired, a second locking ring can be provided at a second end portion of the stent. The locking rings may each include an elevated locus of wires which forms a barb. The barb provides additional strength and sharpness to the locking ring when used to anchor the graft within a blood vessel. The stent is preferably coated or lined with a porous bio-compatible material to allow tissue ingrowth. A preferred method of manufacture comprises inserting a braid into a tube having a smaller diameter than the braid, with one or both of the end portions of the braid extending outside the tube, and precipitation hardening the braid in this configuration in order to form a stent having a body portion with a first pitch angle and one or two locking ring portions with a larger pitch angle.

24 Claims, 6 Drawing Sheets

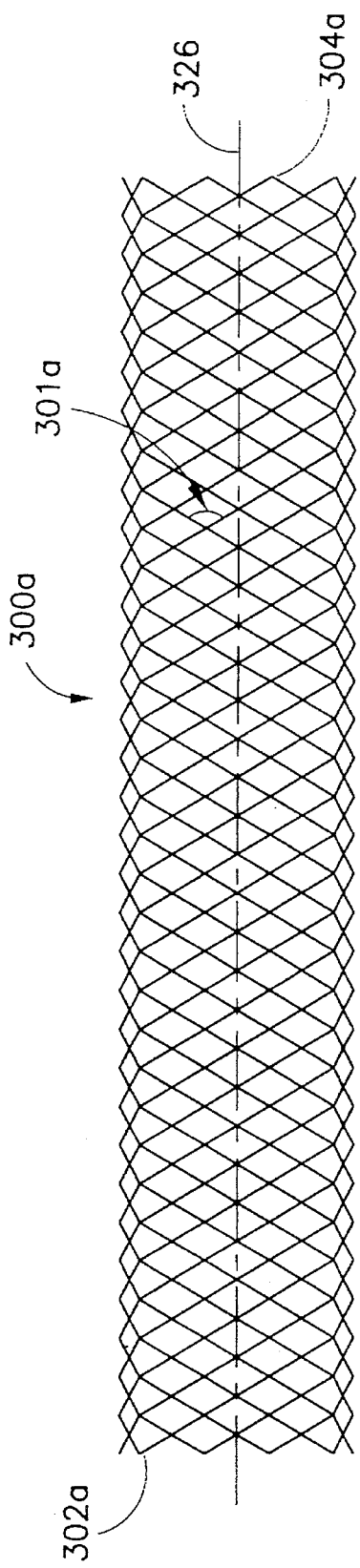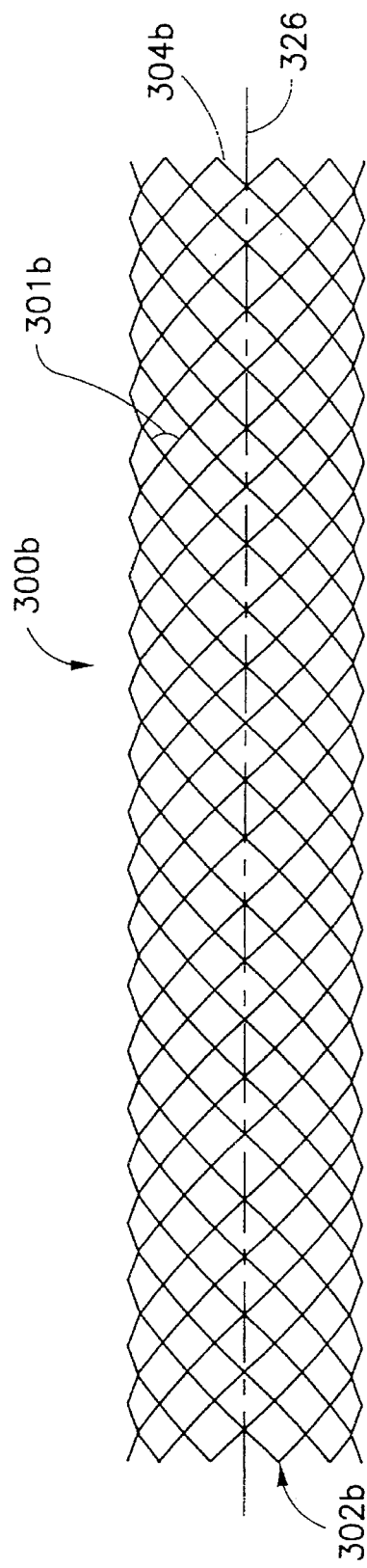
FIG. 3a PRIOR ART
FIG. 3b PRIOR ART

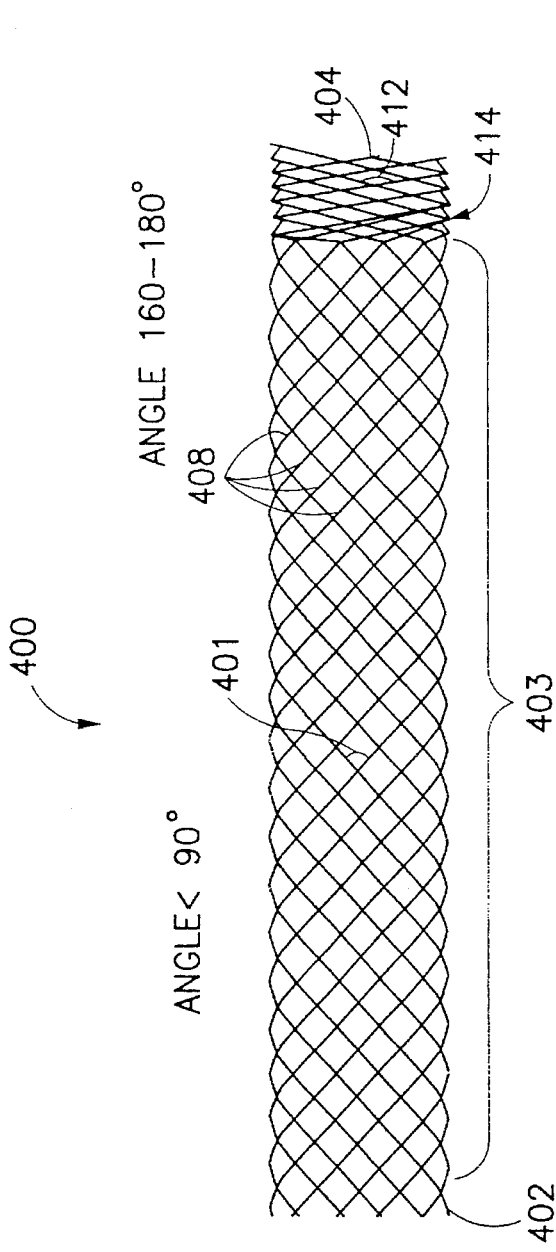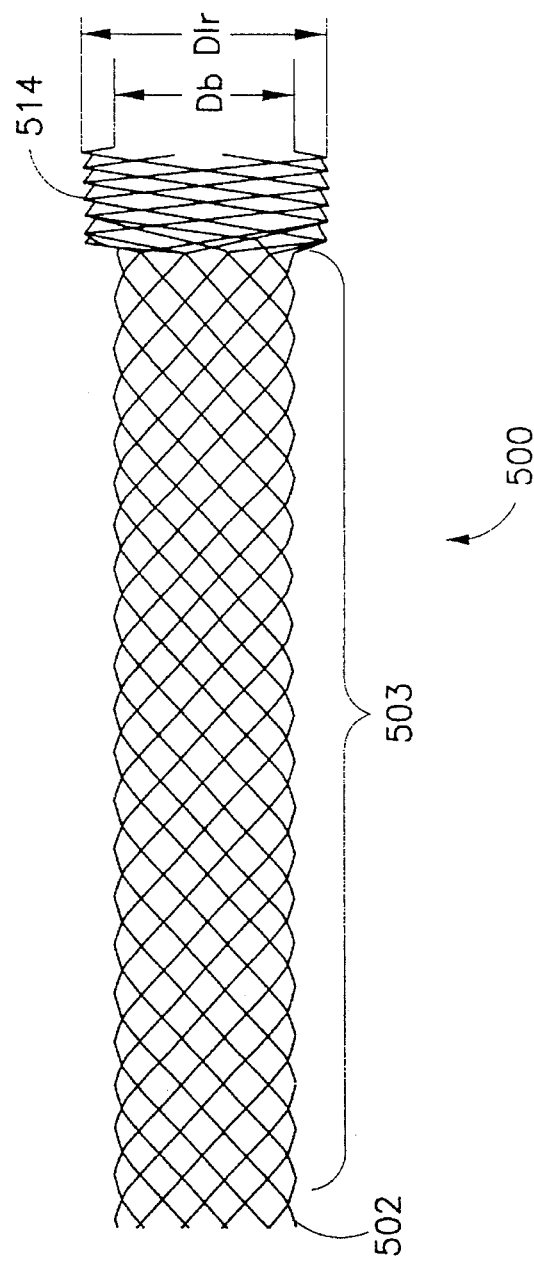

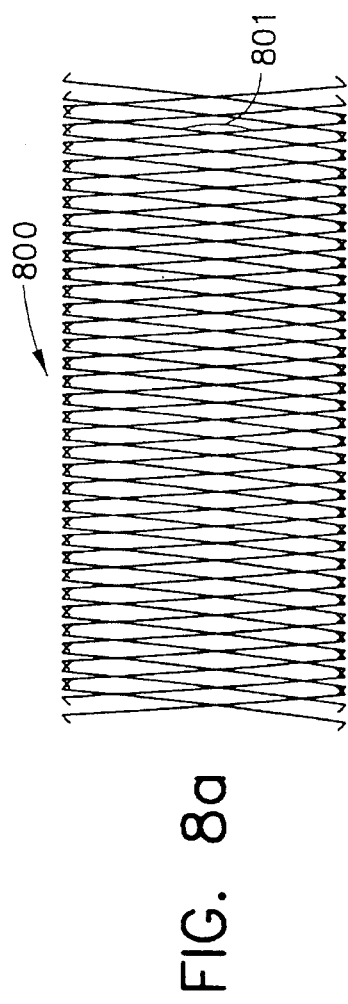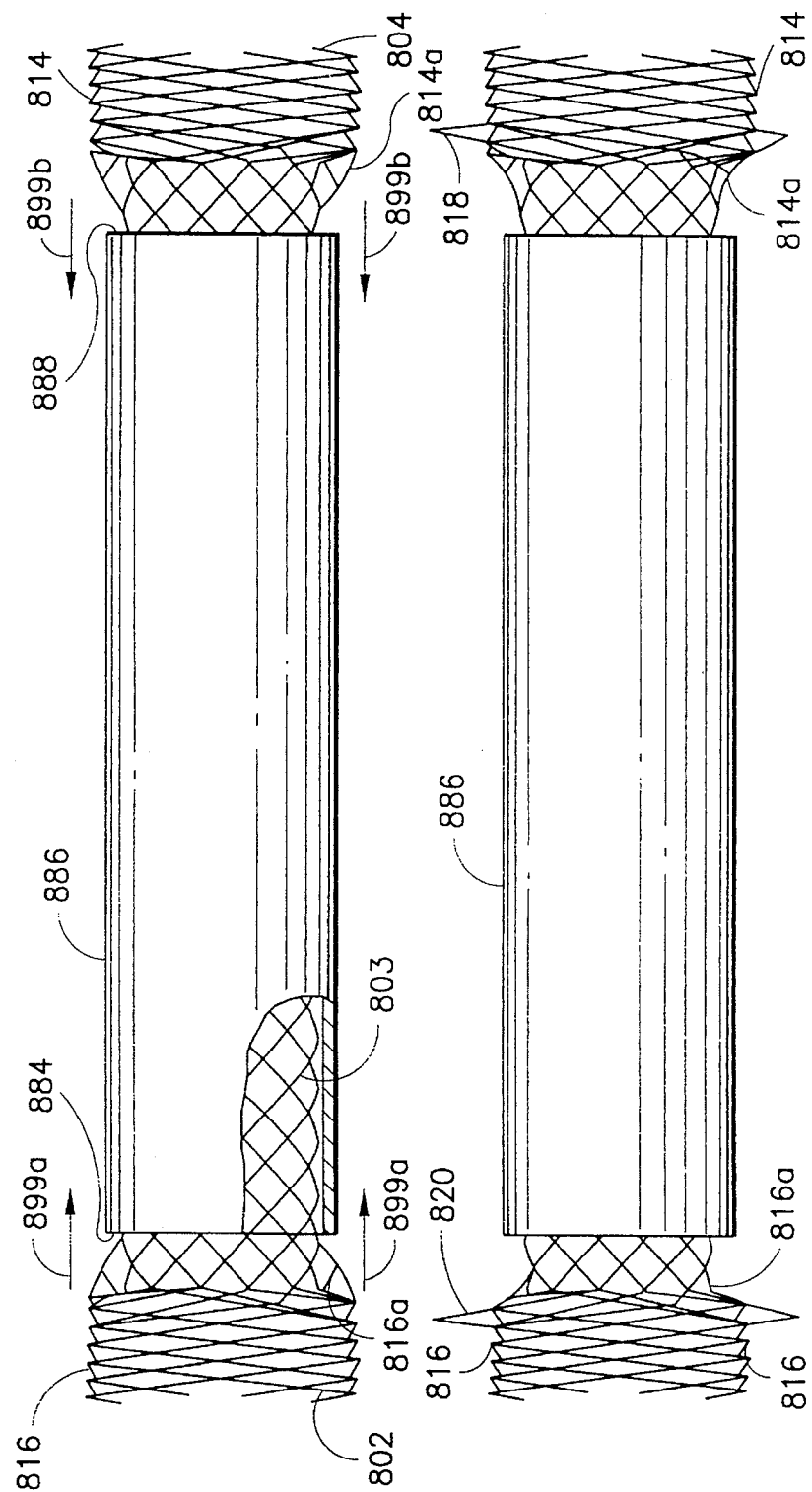

ENDOVASCULAR STENT WITH LOCKING RING

BACKGROUND OF THE INVENTION

1. Field of the Invention

This invention relates broadly to tubular braided stents for use in a body vessel. More particularly, this invention relates to tubular braided stents with endovascular grafts for use in blood vessels.

2. State of the Art

Transluminal prostheses are well known in the medical arts for implantation in blood vessels, biliary ducts, or other similar organs of the living body. These prostheses are commonly known as stents and are used to maintain, open, or dilate tubular structures or to support tubular structures that are being anastomosed. When biocompatible materials are used as a covering or lining for the stent, the prosthesis is called a stent-graft or endoluminal graft. If used specifically in blood vessels, the stent-graft is known as an endovascular graft. A stent may be introduced into the body by compressing or stretching it until its diameter is reduced sufficiently so that it can be fed into a catheter. The stent is delivered through the catheter to the site of deployment and then released from the catheter, whereupon it self-expands. The compression to expansion ratio and radial pressure of stents can usually be determined from basic braid equations. A thorough technical discussion of braid equations and the mechanical properties of stents is found in Jedweb, M. R. and Clerc, C. O., "A Study of the Geometrical and Mechanical Properties of a Self-Expanding Metallic Stent—Theory and Experiment", *Journal of Applied Biomaterials*; Vol. 4, pp. 77–85 (1993). In light of the above, it becomes evident that a stent must possess certain elastic and compression qualities.

A typical state of the art stent, such as disclosed in U.S. Pat. No. 4,655,771 to Wallsten or in U.K. Patent Number 1,205,743 to Didcott, is shown herein in prior art FIGS. 1, 1a, 2, and 2a. The typical stent 10 has a tubular body composed of wire elements 12, each of which extends in a helical configuration about the longitudinal axis 14 of the stent 10. Half of the elements 12 are wound in one direction while the other half are wound in an opposite direction. With this configuration, the diameter of the stent is changeable by axial movement of the ends 9, 11 of the stent. Typically, the crossing elements form a braid-like configuration having a specific pitch angle PA and are arranged so that the diameter of the stent 10 is normally expanded as shown in FIGS. 1 and 1a. Associated with the pitch angle PA is the pitch length PL. The pitch length is measured along the longitudinal axis 14 of the stent 10, and is defined as the distance it takes any wire element 12 of the stent 10 to complete one helical cycle. For example, and as illustrated in prior art FIG. 1a, wire element 32 of the stent 10 begins a helical cycle at the end 11 of the stent 10, and finishes it at line 34, giving the stent 10 a pitch length of PL, which is the distance as measured along the longitudinal axis 14 between the end 11 of the stent 10 and line 34. It will be appreciated from the above, that for any stent of the type illustrated in FIG. 1a, the pitch length PL of the stent is always an inverse function of the pitch angle PA of the stent (for pitch angles in the range 0°–180°). The diameter may be contracted by pulling the ends 11, 13 of the stent 10 away from each other as shown by the arrows 16, 18 in FIG. 2. When the ends of the body are released, the diameter of the stent 10 self-expands and draws the ends 11, 13 of the stent closer to each other. The degree with which the diameter may be contracted is dependent on the pitch angle PA of the crossing elements. Although the Wallsten and Didcott stent designs offer many improvements over the prior art, they still contain several disadvantages discussed in detail below.

Referring to prior art FIGS. 3a, 3b, 3c and 3d the design differences between the Wallsten and Didcott stents are shown. The Wallsten patent discloses a stent 300a (illustrated in FIGS. 3a and 3c herein) with crossing elements forming a pitch angle 301a in the 90° to 160° range. The advantage of these higher pitch angles is that they result in a higher radial force throughout the stent. The radial force is defined as the measure of the outward force that the stent exerts on the vessel into which it is deployed. For example, if a Wallsten type stent is made of thirty-six strands of 0.23 mm (0.009") diameter wire with a Young's modulus (Y=tensile stress/lengthwise strain) of 2.07 Mbar (30 Mpsi), a rigidity modulus of 0.93 Mbar (12 Mpsi) and a yield strength of 24.82 Kbar (360 Kpsi), the radial force outward according to standard braid equations would be approximately 30,000 Pascals when fully compressed.

Another advantage inherent in higher pitch angle stents is that the ends of a high pitch angle stent do not tend to narrow when placed in short aneurysmal necks. In particular, an aneurysm is a blood vessel which has undergone a permanent dilatation, usually caused by a weakening of the vessel wall. An aneurysm typically takes on a sac-like shape with an entrance neck and an exit neck which are connected to other non-aneurysmal blood vessels. When a stent is placed in an aneurysm 350 near a renal artery 398, as illustrated in FIGS. 3c and 3d, the stent takes on one of two different configurations depending on its braid pitch angle and pitch length; i.e., its "periodicity". A high pitch angle stent 300a (having conversely a short pitch length) such as seen in FIG. 3c, when placed in an aneurysm 350 expands evenly from one end 302a to the other 304a. As a result, the stent 300a is locked into place, and the necks 352, 354 of the aneurysm 350 are kept open by the pressure exerting ends 302a, 304a of the stent 300a. In particular, the ends 302a, 304a of the stent 300a are oriented away from the longitudinal axis 326, i.e., flared, and thus aid in affixing the stent 300a to the necks 352, 354 of the aneurysmal vessel 350. The affixed stent 300a is then prevented from moving down the vessel where it could potentially occlude side vessels or even perforate the vessel wall. It can be shown mathematically, that in order for a stent to seat evenly in an aneurysmal neck, the pitch length of the stent should be less than the diameter of the aneurysmal neck; i.e., to exhibit a desired periodicity effect. In general, this requirement often necessitates that the pitch angle of the stent be greater than 160°.

The Wallsten type stent with the larger pitch angle, however, suffers from several shortcomings. Due to the high pitch angle and associated radial force, the Wallsten stent undergoes a large axial elongation upon radial compression. For example, a Wallsten stent with a 160° pitch angle will undergo a 467% elongation upon an 82% diameter contraction. In other words, in order to place a 10 cm long stent of the Wallsten design having a 25 mm diameter in a 25 mm vessel with a catheter having an internal diameter of 4.5 mm, would require the catheter to be approximately 0.5 meter in length. Placement of a stent with this tremendous elongation and radial force is very difficult for several reasons. First, the stent would have to be pushed out of the catheter over a very long distance, which may be extremely difficult in light of the increased friction forces and various bent sections encountered in the catheter as it traverses a tortuous path. Second, the stent will shrink significantly in length as its diameter expands, thereby rendering it difficult to accurately place it in a vessel. The importance of extreme accuracy in placement of an endovascular graft will be appreciated by those knowledgeable in the art. For example, in aneurysmal vessel disease, such as that encountered in the abdominal aorta where the distance between the renal arteries and the aneurysm is quite short (less than 3 cm), misplacement of an endovascular graft over the renal arteries can prove fatal. Similarly, misplacement of the stent openings in the aneurysm can also prove detrimental. Another disadvantage of the Wallsten design, is that the coating material which provides the graft component of the endovascular graft must be able to elongate with the stent several times (e.g. 4 to 5 times) its normal length. There are few graft materials that can undergo this extent of elongation without tearing. In practice, virtually all of the stents made according to Wallsten must have an angle of less than 120°, simply to facilitate placement in the body and minimize the aforementioned problems. Yet another disadvantage of the Wallsten design is that in bridging aneurysms with endoluminal grafts, longitudinal pressure is important in order to seat the graft in the necks of the aneurysm. However, stents with a high pitch angle such as Wallsten do not provide large longitudinal pressures.

The Didcott stent 300b (illustrated in FIGS. 3b and 3d herein), on the other hand, does not have the excessive elongation to contraction ratio associated with the Wallsten stent. Due to the suggested acute pitch angle 301b associated with the Didcott stent, the Didcott stent has the advantage of undergoing only a relatively small axial extension when contracted for introduction through a catheter. For example, for a stent of the same design and having the same dimensions as the Wallsten stent above, but made with a pitch angle of 90°, the Didcott stent will contract from a 25 mm diameter to a fit in a catheter having an internal diameter of approximately 4.5 mm with a resulting axial elongation of only 4 cm. Thus, the stent undergoes only a 40% elongation upon a 82% diameter contraction. The advantage of smaller elongation, however, comes with the disadvantage of providing a significantly weaker radial force than the Wallsten stent. For the same thirty-six strands of 0.23 mm diameter (0.009") wire described above, the Didcott stent has a radial force when fully compressed of only 8,000 pascals.

Another disadvantage of the Didcott low pitch angle stent design is that the ends 302b, 304b of the stent 300b have more of a tendency to perforate the arterial wall of an artery into which the stent is placed because the end wires of the stent 300b are pointed more towards the longitudinal axis of the stent with a slight flare 306b to the outside. With such an arrangement, the hydraulic force of the passing blood flow tends to force the stent downstream, pushing the sharp ends of the stent wires into the blood vessel wall. If enough wire is forced into the vessel wall, the wall can perforate. Yet another disadvantage of the Didcott design relates to when the stent is placed in an aneurysm with a short neck. Because of the periodicity of Didcott, i.e., a low pitch angle and a large pitch length, the Didcott stent undesirably tends to close in the aneurysm neck.

Additional disadvantages are shared by all prior art stents, including both the Didcott and the Wallsten stents. For prior art stents which all have substantially homogeneous pitch angles, the radial load or force (the radial load is proportional to the radial pressure, which is a measure of the outward force that the stent exerts on the vessel into which it is deployed) in the middle of the stent is always greater than the radial force or load at the ends of the stent. This inequality is due to the fact that the stent wires in the middle of the stent are supported on both sides while the wires on the end of the stent only have one side for support. For example, a stent made with 36 wires of 0.009" Elgiloy braided at a homogeneous pitch angle of 75° and with a 25 mm diameter has a radial load in the center of the stent of 0.62 lb. and at the ends of the stent of 0.14 lb. when at 50 percent compression. This discrepancy in radial force can cause the stent to take on a cigar or football-like shape in a vessel. The ensuing constriction of the ends of the stent can subsequently lead to occlusion of the stent, especially in small diameter vessels where any change in cross-sectional area is very significant. Furthermore, when dealing with an aneurysm, a stent cannot be anchored to the walls of a vessel by its body section as the vessel walls are either damaged and thin or missing. Anchoring at the ends would be equally unfeasible in light of the above described discrepancy in radial force and resulting cigar-like shape of the stent. Thus, the prior art stents cannot advantageously be used in those situations where the stent must be locked in a particular position and the walls of the body cavity in which the stent is inserted cannot provide anchoring means.

SUMMARY OF THE INVENTION

It is therefore an object of the invention to provide a stent or endovascular graft with a low longitudinal elongation and a high radial pressure.

It is also an object of the invention to provide a stent or endovascular graft with end radial pressure equal or greater than the middle radial pressure.

It is a further object of the invention to provide a stent or endovascular graft with one end which can an be anchored to the walls of a body lumen.

It is another an object of the invention to provide a stent or endovascular graft with ends which can stay open in a calcified lumen.

A further object of the invention is to provide a stent or endovascular graft which does not perforate the walls of a body lumen.

Another object of the invention is to provide a stent or endovascular graft which maintains a cylindrical shape even when the vessel in which it is located undergoes constriction.

An additional object of the invention is to provide a stent having at least a portion with a pitch length less than the neck diameter of an aneurysm.

It is yet another object of the invention to provide a stent or endovascular graft which contains a barb for affixing the stent or endovascular graft into a blood vessel wall.

Even another object of the invention is to provide a stent or endovascular graft which simultaneously provides large longitudinal and radial pressures.

According to the invention, a braided stent, preferably having a coating of a porous material to form an endovascular graft is provided. The stent is primarily of a braided structure of the Didcott design, with a pitch angle of less than or equal to 90°, preferably 70° to 90°. However, at least one end portion of the stent has a locking ring which is comprised of a relatively short braid segment with a very obtuse pitch angle. The diameter of the locking ring is preferably equal to or greater than the diameter of the main body portion of the stent. As a result of its higher pitch angle, the locking ring has a greater radial force than that of the rest of the stent.

In a preferred embodiment the locking ring section of the stent further includes an elevated locus of wires which act as a barb. The barb provides additional strength and sharpness to the locking ring when used to anchor the graft within a blood vessel. Additional preferred aspects of the stent include: providing the locking ring section with a pitch angle between 140° and 180°; providing a length ratio between the stent body portion and the locking ring portion of between two to one and nine to one; and providing the locking ring portion with a diameter which is at least equal to and up to two times greater than the diameter of the stent body portion.

In order to provide an endovascular graft, the stent is coated or lined with a porous bio-compatible material which allows tissue ingrowth throughout the length of the stent. Preferred coating materials include polyurethane, spun polyurethane, spun polycarbonate urethane, spun polyolefin, silicone coated polyurethane, spun silicone and various combinations of the above. Also included are those materials rendered porous by spray techniques, phase inversion, electrostatic spinning, or particle elution which may also be biodegradable or filled with medicinal drugs.

The preferred coating may be applied by spinning it at an angle coincident with the pitch angle of the stent. It is important to match the coating angle with both the angle of the body section of the stent and of the locking ring ends of the stent to enable proper contraction of the stent or axial elongation. The coating can then be bonded to the stent in many different ways. For example, an inner lining or coating can be first spun on a mandrel, after which a stent covered with an adhesive substance is pulled down on the lining, and then the adhesive is cured or dried. Alternatively, the stent can first placed over the lining and more coating material spun over the stent. The coating, while wet, can then be pressed through the interstices of the stent and bonded to the underlining coating, thereby capturing the stent. Another alternative is to place the stent on a mandrel, spray or pad a thin coating of polyurethane lacquer or other adhesive such as silicone rubber or epoxy and the like over the stent, and then spin the coating over the lacquer which will then bond the coating to the stent once the lacquer or adhesive dries or is cured.

The method of manufacturing a stent with a locking ring and barb according to the invention comprises braiding together multiple resilient metal wires of desired diameter and geometry on a mandrel. The braid is then removed from the mandrel where the natural recoil in the braid causes it to shorten and expand and its pitch angle to increase. The braid is then stretched and inserted into a tube having a diameter smaller than that of the braid, such that only the end of the braid is outside the tube and the rest of the braid is compressed to the internal diameter of the tube. It will be appreciated that the diameter of the body portion of the braid inside the tube is such that the pitch angle of the wires is preferably less than 9°. The non-compressed end, which will form a locking ring after heat treatment, has a pitch angle greater than the compressed body portion. If desired, the locking ring portion may be pushed laterally in order to deform the wires and to create an outer barbed section adjacent to the compressed body portion. The braid is then heat treated in this configuration and precipitation hardened at appropriate temperatures to form the stent. The hardened braid or stent is then pulled out of the tube, at which point it rebounds slightly and settles into its new non-compressed stent configuration with a barb at the locking ring end. For configurations which require that the locking ring diameter be approximately equal to that of the body of the stent, the pitch angle of the stent must be increased during the braiding process. This increase in pitch angle is done by slowing down the motion of the braid mandril in relation to the carrier speed.

If desired, stents with locking rings on each end may be formed by following the same method of manufacture, but permitting both end portions of the braid to extend outside the tube. Also, if desired, instead of inserting the braid into a tube such that an end portion of the braid remains outside the tube, the tube may be formed with a stepped diameter such that the entire braid fits inside the tube, but assumes a stepped configuration.

Additional objects and advantages of the invention will become apparent to those skilled in the art upon reference to the detailed description taken in conjunction with the provided figures.

BRIEF DESCRIPTION OF THE DRAWINGS

FIG. 3a is a broken side view of an expanded prior art stent according to the Wallsten design;

FIG. 3b is a broken side view of an expanded prior art stent according to the Didcott design;

FIG. 4 is a broken side elevation view of a first embodiment of the stent according to the invention;

FIG. 5 is a side elevation view of a second embodiment of the stent according to the invention;

FIGS. 8a–8c are side elevation views of the stent of the invention during different steps of manufacture;

DETAILED DESCRIPTION OF THE PREFERRED EMBODIMENT

Figure 1:
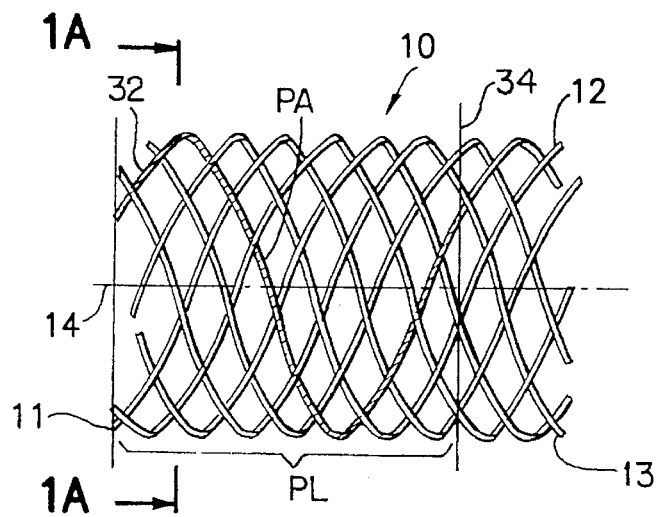
FIG. 1 is a broken side elevation view of a prior art stent expanded in a non-stressed position.
Figure 1A:
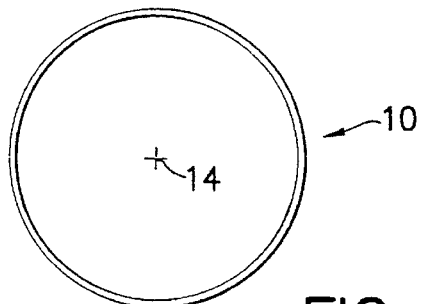
FIG. 1a is a cross sectional view along line 1A—1A of FIG. 1.
Figure 2:
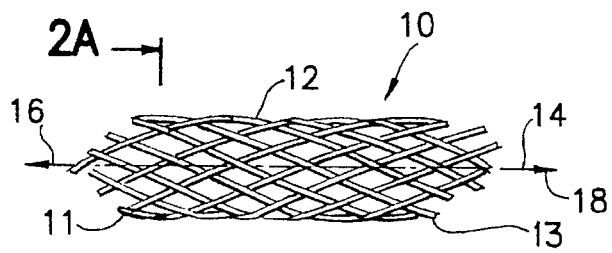
FIG. 2 is a broken side elevation view of a prior art stent stretched and contracted.
Figure 2A:
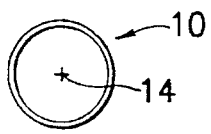
FIG. 2a is a cross sectional view along line 2A—2A of FIG. 2.
Figure 3C:
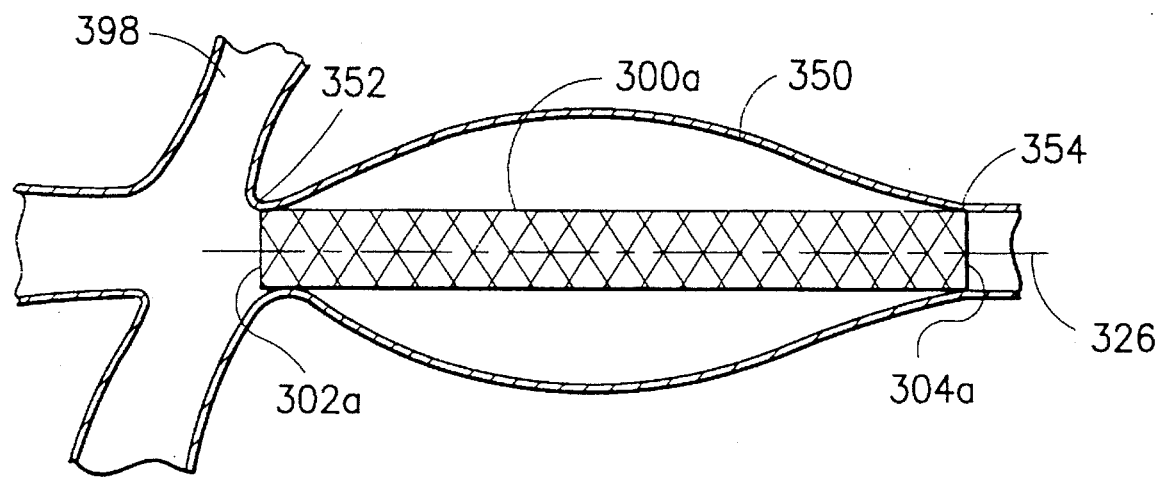
FIG. 3c is a side view of an expanded prior art stent according to the Wallsten design when placed in a blood vessel aneurysm.
Figure 3D:
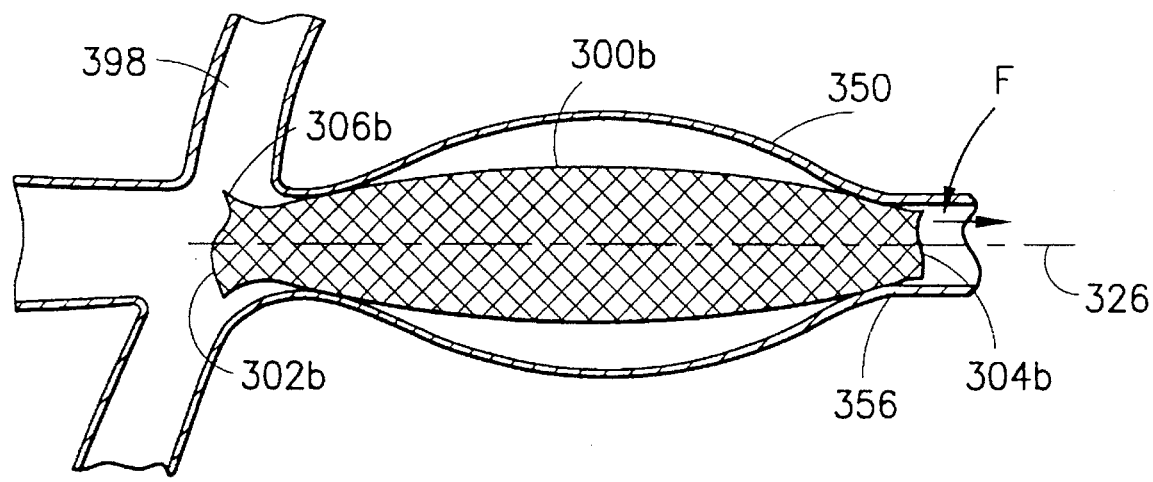
FIG. 3d is a side view of an expanded prior art stent according to the Didcott design when placed in a blood vessel aneurysm.

Turning to FIG. 4, a first embodiment of the endovascular stent 400 of the invention is shown. The stent 400 includes a plurality of cross-helically wound wire elements 408 which define a tubular body portion 403 with first and second ends 402, 404. The crossing wire elements 408 of the body section 403 form a body pitch angle 401 which is preferably less than or equal to 90°; and preferably in the 70° to 90° range. At the second end 404, the crossing elements 408 form a second end pitch angle 412 which is typically greater than 90° and preferably in the 140° to 180° range, and which results in a locking ring 414. The locking ring 414 has a greater pitch angle than the body portion 403, and a radial force which exceeds that of the body portion 403 of the stent 400. The ratio of the length of the body portion 403 to the length of the locking ring portion 414 is preferably on the order of nine to one. For example, if the stent 400 were constructed to have a length of 10 cm and a diameter of 25.00 mm, the body portion 403 of the stent 400 preferably would be about 9.00 cm long and the locking ring portion 414 would be about 1.00 cm long. If the body portion 403 is given a pitch angle 401 of 90° and the locking ring 414 is given a pitch angle 412 of 160°, the stent 400 would extend an additional 5.40 cm when the diameter of the stent is fully contracted to 4 mm, representing only a 54% extension in the length of the stent 400. In the same example, the locking ring 414 has an outward radial pressure when fully compressed of 30,000 Pascals and a middle radial pressure of 9,500 Pascals. This braid construction enables the stent 400 to be placed relatively easily in a body cavity, as it requires a relatively short catheter. In addition, due to the design having a change in pitch angle, the stent 400 can be securely anchored by the locking ring 414 to the wall of a vessel (not shown). It will be appreciated that, as the locking ring 414 of the stent 400 has a pitch angle of about 160°, the stent 400 can advantageously be deployed in an aneurysm, as the locking ring 414 will lock into place within the neck of the aneurysm in a desired manner. In addition, because the body portion 403 of the stent has a pitch angle of about 90°, the desired longitudinal forces are obtained which further helps seat the stent in the necks of the aneurysm.

Referring now to FIG. 5, a second embodiment of an endovascular stent 500 of the invention is shown. The stent 500 is substantially similar to the stent 400 shown in FIG. 4 and generally includes a body portion 503 having a body diameter Db and a locking ring 514 having a locking ring diameter Dlr. Unlike the first embodiment, however, the locking ring diameter Dlr is larger than the diameter of the body portion Db. The preferred ratio of the locking ring diameter to the body diameter (Dlr/Db) ranges from 1 to 2, and is most preferably between 1.0 and 1.3. The advantage of the larger locking ring diameter is that it provides for a more secure anchor and a funnel-like entrance into the endoluminal graft.

Figure 6:
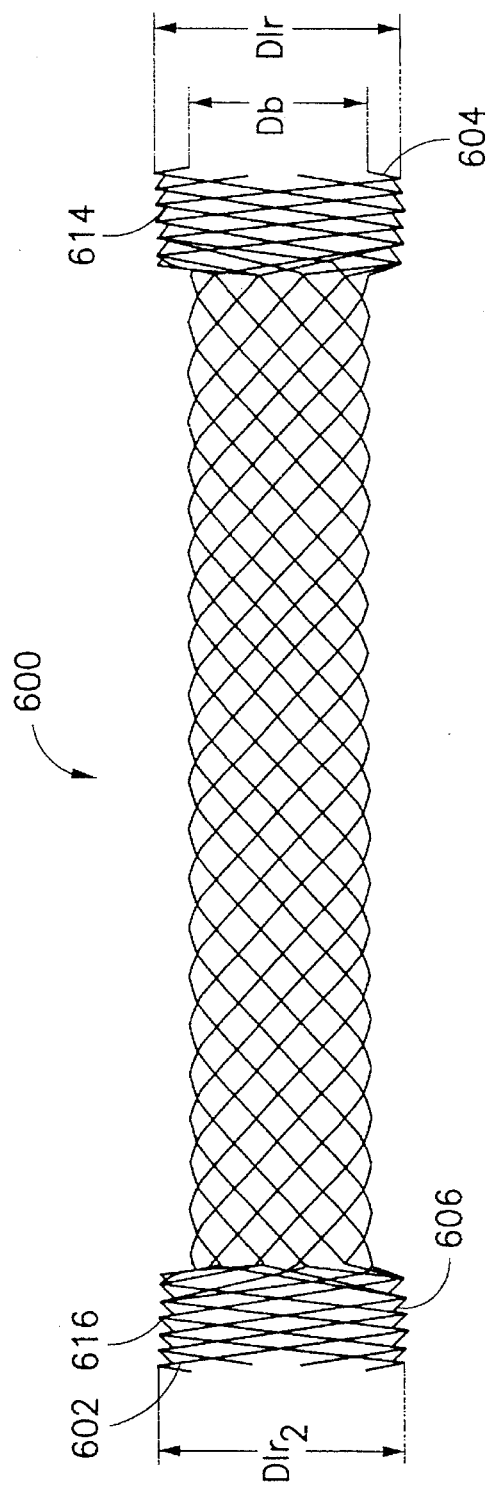
FIG. 6 is a side elevation view of a third embodiment of the stent according to the invention.

Turning now to FIG. 6, a third preferred embodiment of an endovascular stent 600 of the invention is shown. The stent 600 is substantially similar to the stent 500 described with reference in FIG. 5, but further includes a second locking ring 616 at the first end 602 of the stent 600 in addition to the first locking ring 614 at the second end 604. The diameter Dlr2 of the second locking ring 616 is preferably equal to the diameter Dlr of the first locking ring 614 and the preferred ratio of the locking ring diameters Dlr, Dlr2 to the body diameter Db ranges from 1 to 2, and is most preferably between 1.0 and 1.3. When the stent 600 is provided with a biocompatible coating to form an endovascular graft, the presence of the two stepped up locking rings 614, 616 helps the graft seat in the blood vessel and seal. This embodiment has an advantage over the single locking ring stents of the first and second embodiments described above (see FIGS. 4 and 5) in that it can be used in the presence of calcified plaque protruding from the lumen of the blood vessel which would otherwise prevent an endovascular graft with only one locking ring from opening entirely. A second advantage of sealing both ends of the endovascular graft to the vessel walls, is that it insures that both ends of the endoluminal graft will remain wide open.

Figure 7:
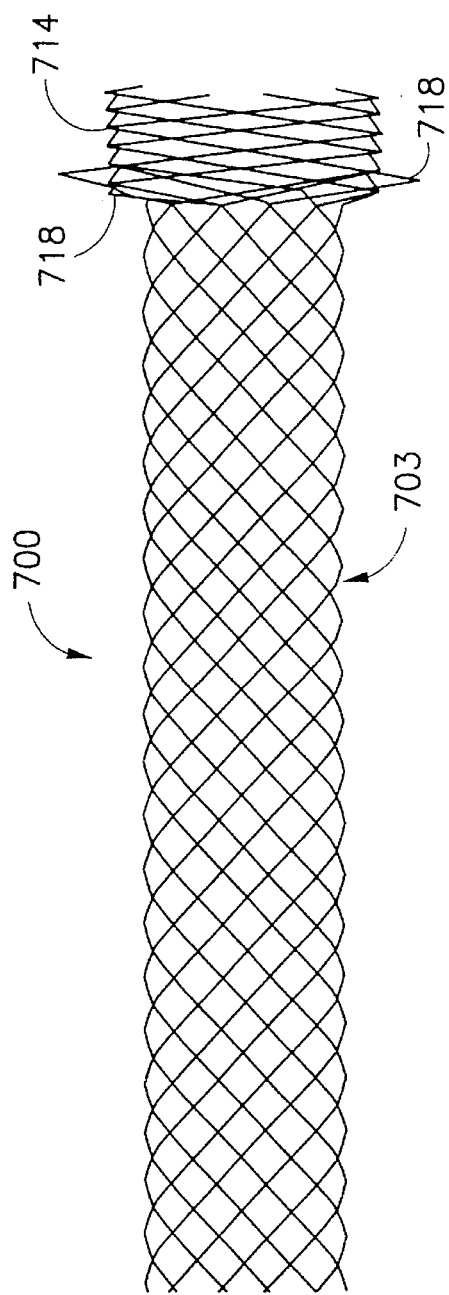
FIG. 7 is a side elevation view of a fourth embodiment of the stent according to the invention.

A fourth embodiment of the endovascular stent 700 of the invention is seen in FIG. 7. The stent 700 is substantially similar to the stent 500 described with respect to FIG. 5, except that the locking ring 714 of the present embodiment 700 further includes an elevated locus of wires 718 at the locking ring 714 location which act as a barb. The addition of the barb 718 to the locking ring 714 provides for easier and better anchoring of the stent as well as greater anchoring strength. The barb 718 essentially digs into the wall of an artery in which the stent 700 is being deployed and forms a secure seal and anchoring mechanism. Although the locking ring 714 with the barb 718 is shown here to have a larger diameter than the diameter of the body portion 703 of the stent, the diameters may be made substantially the same if desired.

Each of the above described embodiments of the invention may be made into endovascular grafts by coating or lining the stent with a porous bio-compatible material to allow tissue ingrowth throughout the stent length. Preferred coating materials include polyurethane, spun polyurethane as described in U.S. Pat. No. 4,475,972 to Wong, spun polycarbonate urethane as described in U.S. Pat. No. 5,133,742 and 5,229,431 to Pinchuk, or silicone coated polyurethane as described in U.S. Pat. No. 4,851,009 to Pinchuk. Other materials such as spun silicone rubber or polyurethane silicone and silicone rubber rendered porous by spray techniques, phase inversion, electrostatic spinning, or particle elution, may also be used to provide these coatings.

It will also be appreciated that the coatings on the stent or the stent itself can be used to deliver drugs such as anticoagulants, thrombolytic therapies, steroids, etc. or other substances such as radioactive isotopes, actinic radiation or monoclonal antibodies and the like, to the deployment site. These drugs or other substances may reduce thrombosis by interfering with the coagulation of blood. In addition, they may provide better ingrowth of natural tissue, or they may reduce the proliferation of smooth muscle cells and lessen neointimal hyperplasia. It can also be appreciated, that these devices can be seeded with cells such as endothelial cells, or with genetically engineered cells, and the like, to limit thrombosis, neointimal hyperplasia and generally to increase the biocompatibility of the system.

Similarly, the surfaces of these devices may be coated with sodding chemistries, such as fibronectin, laminum, glycoaminoglycans, or other proteins and the like, to attract and secure (adhere) cells and cellular substances which may further enhance the hemocompatibility of the device. In addition, the stent or coating can be maintained highly porous as provided by the spinning of fibers, or the porosity can be reduced significantly to provide somewhat leak proof coatings or microporous coatings. Such leak proof coatings can be achieved by impregnating the coating with gelatin, collagen, albumin, hydrogels, and the like, and then substantially crosslinking them with crosslinkers, such as formaldehyde, glutaraldehyde, polyglycidyl ethers, and the like, as are normally used in the art for such purposes. The coatings may also be fabricated from biodegradable substances such as polylactide, polyglycolide, polyether or polyester urethanes, polyanhydrides, gelatin, albumin, collagen, chitin, cellulose, etc., which are eventually absorbed by the body and replaced with natural tissue. Enhanced biocompatibility may be provided by replacing the stent coatings directly with natural tissue, such as by attaching biological tissue from arteries and veins, or facia or pericardium. In addition, the stent can be implanted into animals for a time sufficient for the biological host tissue to ingrow into the stent, as is well known in the art as the "Sparks Mandril" technology. The stent with ingrown tissue is then harvested, crosslinked to render it non-immunogenic, and implanted with such crosslinked tissue coatings into the patient.

Once a coating type is selected, it is preferably applied in a specific manner. In particular, the coating is preferably spun at an angle coincident with the pitch angle of the stent, with the coating angle matched with both the angle of the body section of the stent and of the locking ring ends of the stent. It is usually preferable to coat the entire stent, as coating only the body of the stent may allow leakage of blood to the exterior of the stent when it is deployed in a blood vessel.

The coating can be bonded to the stent through the use of many different methods. For example, an inner lining or coating can be first spun on a mandrel, after which a stent covered with an adhesive substance is pulled down on the lining and then the adhesive is cured, melted and solidified or dried. Alternatively, the stent can first be placed over the lining and more coating material spun over the stent. The coating, while wet, can then be pressed through the interstices of the stent and bonded to the underlining coating, thereby affixing it to the stent. Another alternative is to place the stent on a mandrel, apply (e.g., spray, dip, pad, etc.) a thin coating of polyurethane lacquer over the stent, and then spin the coating over the lacquer so that it is bonded to the stent once the lacquer dries. In yet another alternative, the stent itself may be repeatedly coated by dipping it in a lacquer to build up a porous membrane using particle elution and phase inversion techniques.

Turning now to FIGS. 8a–8c, the preferred method of manufacturing a stent with a locking ring and barb is shown. A braid 800 is formed by braiding, e.g., thirty-six wires of 0.23 mm (0.009") diameter Elgiloy wire on a 1.25" mandril (not shown) with a pitch angle of 110°. The braid 800 is then removed from the mandrel where the natural recoil of the braid causes it to shorten and expand to approximately 3.81 cm (1.5") in diameter, with the pitch angle 801 naturally increasing to between 150° and 180° as shown in FIG. 8a. The above is a natural tendency for braids comprised of spring steel which are not heat treated on the mandrel. The braid 800 is then pulled down on one end and inserted through one end opening 884 of a tube 886 and out the other end 888 of the tube 886. The tube 886 has an internal diameter smaller than the diameter of the non-compressed braid, (e.g. 1.73 cm (0.68")), such that the body portion 803 of the braid 800 is compressed to the internal diameter of the tube 806, and the two ends 802, 804 of the braid 800 maintain the diameter of the braid 800 when non-compressed; thereby forming first and second locking rings 814, 816 as seen in FIG. 8b. The non-compressed locking ring portions 812, 814, are respectively pushed longitudinally in the directions of arrows 899a and 899b, so as to deform the wires. In other words, force is applied such that the wire in the flared parts 814a, 816a of the rings 812, 814 is pushed out circumferentially to form two ripples or barbs 818, 82- as seen in FIG. 8c. The braid 800 is then heat treated in the configuration of FIG. 8c to form a stent. Metals such as Elgiloy wire are best precipitation hardened at temperatures in the 400° to 600° Centigrade range, for one to five hours in an inert atmosphere. Those well versed in the art of metallurgy will understand how to precipitation harden cobalt-chromium-nickel compounds. The hardened stent is then pulled out of the tube 806, at which point the braid rebounds slightly and settles into its new non-compressed configuration which resembles the embodiment of the invention as illustrated in FIG. 7, with the addition of a second locking ring and barb.

One alternate way of making the locking rings 814, 816 is to braid the braid at two different angles. For example, the body portion 803 can be braided at a 90° pitch angle and the locking ring portions 812, 814 at a 160° pitch angle. As another alternative, the locking ring portions 812, 814 of the braid 800 can be braided on a stepped portion of the mandrel which has a stepped or barbed profile. The braid can also be heat treated on two different sized mandrels, or stepped/ barbed mandrels to provide the locking ring configuration. The ratio of the stent locking ring diameters to the stent body portion diameter dictates the relative angles at which the locking ring is braided in relation to the body of the stent.

Yet another alternative manner of making the locking rings 814, 816, is to provide a tube such as tube 886 with a stepped diameter. The larger diameter portion(s) of the tube would be used to house the locking ring portion(s) of the braid, and could cause the end portion(s) of the braid to be slightly compressed, or could permit the end portion(s) of the braid to assume a full non-compressed position.

There have been described and illustrated herein several embodiments of a tubular braided stent and a method of manufacturing the stent of the invention. While particular embodiments of the invention have been described, it is not intended that the invention be limited thereto, as it is intended that the invention be as broad in scope as the art will allow and that the specification be read likewise. Thus, while particular stent designs have been disclosed, it will be appreciated that other designs may work as well. For example, while stents having end locking rings have been disclosed, stents with locking rings along the body of the stent can also be used. Furthermore while particular pitch angles for the body and end sections of the stent have been disclosed, it will be understood that any stent having larger pitch angles at the end sections than the body section may be used as well. Also, while particular bio-compatible coatings have been disclosed, it will be recognized that any other suitable bio-compatible coating may be used. In addition, while particular methods of coating the stent have been disclosed, it will be understood by those skilled in the art that any other method may be used that matches the coating angle with the pitch angle of the stent. Moreover, while particular configurations have been disclosed in reference to the dimensions and shape of the endovascular graft, it will be appreciated that other configurations could be used as well. Furthermore, while a particular method of manufacturing the endovascular graft of the invention has been described, it will be understood that any manufacturing method can be similarly used which results in providing a larger pitch angle for the stent locking rings. It will therefore be appreciated by those skilled in the art that yet other modifications could be made to the provided invention without deviating from its spirit and scope as so claimed.

I claim:

1. A prosthetic device for implantation in a body cavity of a living body, comprising:

a braided stent formed from a first plurality of resiliently-deformable wires helically wound in a first direction and a second plurality of resiliently-deformable wires helically wound in a second direction opposite said first direction and crossing said first wires, said stent having a first cylindrical body portion with said first and second wires crossing at a base pitch angle, and a first substantially cylindrical end portion where said first and second wires cross at a first end portion pitch angle, wherein, said first end portion pitch angle is substantially greater than said base pitch angle producing greater radial force than that of said body portion.

2. A prosthetic device according to claim 1, wherein: said base pitch angle is less than or equal to 90°.

3. A prosthetic device according to claim 2, wherein: said base pitch angle is between 70° and 90°.

4. A prosthetic device according to claim 1, wherein: said first end portion pitch angle is greater than 90°.

5. A prosthetic device according to claim 4, wherein: said first end portion pitch angle is between 140° and 180°.

6. A prosthetic device according to claim 1, wherein:

said base pitch angle is equal to or less than 90° and said first end portion pitch angle is between 140° and 180°.

7. A prosthetic device according to claim 6, wherein:

said base pitch angle is between 70° and 90°, and said first end portion pitch angle is between 160° and 180°.

8. A prosthetic device according to claim 1, wherein:

said body portion has a body portion diameter, said first end portion has a first end portion diameter, and said stent has a second end portion having a second end portion diameter, and at least said first end portion diameter is different from said body portion diameter.

9. A prosthetic device according to claim 8, wherein:

said first end portion diameter and said second end portion diameter are greater than said body portion diameter.

10. A prosthetic device according to claim 9, wherein:

a ratio of said first end portion diameter to said body portion diameter is between 1 and 2.

11. A prosthetic device according to claim 10, wherein:

a ratio of said first end portion diameter to said body portion diameter is between 1 and 1.3.

12. A prosthetic device according to claim 1, wherein:

said stent has a second end portion having a second end portion pitch angle which is greater than said base pitch angle.

13. A prosthetic device according to claim 12, wherein:

said second end portion pitch angle substantially equals said first end portion pitch angle.

14. A prosthetic device according to claim 1, wherein:

said first end portion includes a braided elevated section located at a location other than at a very end of said prosthetic device and having a diameter larger than a diameter of the remainder of said first end portion, thereby forming a barb.

15. A prosthetic device according to claim 6, wherein:

said first end portion includes a braided elevated section located at a location other than at a very end of said prosthetic device and having a diameter larger than a diameter of the remainder of said first end portion, thereby forming a barb.

16. A prosthetic device according to claim 1, wherein:

said stent is coated or lined with a porous bio-compatible graft material.

17. A prosthetic device according to claim 16, wherein:

said porous bio-compatible graft material is one of a polyurethane, a spun polyurethane, a spun polycarbonate urethane, a spun silicone, and a spun polyolefin.

18. A prosthetic device according to claim 1, wherein:

said first end portion is stepped relative to said body portion with said body portion having a first diameter, and said first end portion having a second diameter substantially different than said first diameter.

19. A prosthetic device according to claim 18, wherein:

said second diameter is greater than said first diameter.

20. A prosthetic device according to claim 19, wherein:

a ratio of said second diameter to said first diameter is less than 2.

21. A prosthetic device according to claim 20 wherein:

said ratio is less than 1.3.

22. A prosthetic device according to claim 18, wherein:

said stent has a second end portion substantially stepped relative to said body portion and having a third diameter substantially equal to said second diameter.

23. A prosthetic device according to claim 18 for implantation in an aneurysm having a neck diameter, wherein:

said first end portion has a pitch length equal to or less than the neck diameter.

24. A prosthetic device according to claim 23, wherein:

said stent has a second end portion substantially stepped relative to said body portion and having a third diameter substantially equal to said second diameter.

* * * * *